US012672877B2

(12) United States Patent
    Cashdan et al.

(10) Patent No.: US 12,672,877 B2
(45) Date of Patent: Jul. 7, 2026

(54) EMBOLIZATION MICROCATHETER FOR DELIVERY OF BEADS TO PERIPHERAL VESSELS

(71) Applicant: Argon Medical Devices, Inc., Plano, TX (US)

(72) Inventors: Judy Cashdan, Hashmonaim (IL); Tom Dagan, Omer (IL); Yuval Zipory, Modiin (IL); Osnat Harbater, Raanana (IL); Eran Miller, Moshav Beit Elazari (IL)

( * ) Notice: Subject to any disclaimer, the term of this patent is extended or adjusted under 35 U.S.C. 154(b) by 100 days.

(21) Appl. No.: 18/699,299

(22) PCT Filed: Oct. 19, 2022

(86) PCT No.: PCT/IL2022/051107
    § 371 (c)(1),
    (2) Date: Apr. 7, 2024

(87) PCT Pub. No.: WO2023/067601
    PCT Pub. Date: Apr. 27, 2023

(65) Prior Publication Data
    US 2024/0423634 A1      Dec. 26, 2024

Related U.S. Application Data

(60) Provisional application No. 63/341,014, filed on May 12, 2022.

(30) Foreign Application Priority Data

Oct. 20, 2021     (IL) ........................................ 287420

(51) Int. Cl.
    *A61B 17/12*        (2006.01)
    *A61M 25/00*        (2006.01)

(52) U.S. Cl.
    CPC .. *A61B 17/12159* (2013.01); *A61B 17/12031* (2013.01); *A61B 17/12109* (2013.01);
                (Continued)

(58) Field of Classification Search
    CPC ........ A61B 17/12159; A61B 17/12031; A61B 17/12109; A61B 2017/1205;
                (Continued)

(56) References Cited

U.S. PATENT DOCUMENTS 6,231,570 B1 *   5/2001   Tu ........................... A61B 18/08
                                                               606/41
8,096,985 B2     1/2012   Legaspi et al.
                (Continued)

FOREIGN PATENT DOCUMENTS

| IL | 276416 A | * | 8/2021 | ........ A61M 25/0053 |
| IL | 276416 B | | 8/2021 | |
| WO | 2021035042 A1 | | 2/2021 | |

OTHER PUBLICATIONS

PCT International Search Report for International Application No. PCT/IL2022/051107 mailed Dec. 22, 2022, 5pp.
                (Continued)

*Primary Examiner* — Richard G Louis
(74) *Attorney, Agent, or Firm* — IPHORGAN LTD.

(57)                ABSTRACT

An embolization microcatheter including an elongated main body and a distal section, the distal section comprising an off-setting portion and a winding portion, wherein the winding portion comprises about half a loop of a three-dimensional spiral, such that a longitudinal axis of the winding portion is offset and/or disposed at an acute angle relative to a longitudinal axis of the elongated main body, and wherein the off-setting portion is disposed at an angle of between about 60° and about 120° degrees relative to the longitudinal axis of the elongated main body.

19 Claims, 14 Drawing Sheets

(52) U.S. Cl.
CPC ...... *A61M 25/001* (2013.01); *A61M 25/0021*
(2013.01); *A61B 2017/1205* (2013.01); *A61M*
*2025/0042* (2013.01)

(58) Field of Classification Search
CPC ... A61B 2017/00738; A61B 17/12186; A61M
25/001; A61M 25/0021; A61M
2025/0042; A61M 25/0054; A61M
25/0068; A61M 25/0041
See application file for complete search history.

(56)                     References Cited

U.S. PATENT DOCUMENTS

2009/0287187 A1*  11/2009  Legaspi ............ A61M 25/0054
                                                              604/523
2013/0123752 A1      5/2013  Pursley

OTHER PUBLICATIONS

PCT Written Opinion for International Application No. PCT/IL2022/
051107 mailed Dec. 22, 2022, 5pp.

\* cited by examiner

EMBOLIZATION MICROCATHETER FOR DELIVERY OF BEADS TO PERIPHERAL VESSELS

This application is a National Phase of PCT Patent Application No. PCT/IL2022/051107 having International filing date of Oct. 19, 2024, which claims the benefit of priority of U.S. Provisional Patent Application No. 63/341, 014, filed May 12, 2022 and Israel application No. 287420 filed on Oct. 20, 2021. The contents of these applications are all incorporated herein by reference in their entireties.

TECHNICAL FIELD

The present disclosure generally relates to the field of microcatheters for embolization, specifically to embolization catheters suitable for navigating within blood vessels for delivery of embolization beads to peripheral blood vessels.

BACKGROUND

Transarterial embolization therapy, tumor embolization, or transcatheter arterial embolization (TAE), involves administration of embolization material (which may include chemotherapeutics or/and radiotherapeutics) directly to a tumor (for example, liver tumors), via a microcatheter.

Embolization of tumors is typically performed utilizing microcatheters due to the requirement for selectively affecting the tumor while preventing, as much as possible, damage to healthy tissue. A major problem associated with embolization is "non-target embolization", where the embolic material travels to blood vessels, other than those directly feeding the target tumor or tumor region, thus damaging healthy tissues, resulting in unpleasant and even hazardous outcomes.

During embolization, the embolization catheter must be advanced and navigate through small and often tortuous vessels. Accessibility to these vessels is difficult, if not precluded, using standard microcatheters. Moreover, tracking the direction of the microcatheter's progress within the blood vessels is limited due to the structure of the microcatheters.

There thus remains a need for microcatheters capable of delivering embolization beads to small and tortuous blood vessels and facilitate navigation and reliable real time tracking during the embolization procedure.

SUMMARY OF THE INVENTION

The present disclosure relates to embolization microcatheters which are suitable for navigation in small and tortuous blood vessels, while also facilitating reliable real time tracking during the embolization procedure.

This is advantageously achieved by the unique structure of the embolization microcatheters, which has an elongated main body and a distal section, which includes an off-setting portion and a winding portion. The winding portion has about half a loop of a three-dimensional spiral, such that a longitudinal axis of the winding portion is offset and/or disposed at an acute angle relative to a longitudinal axis of the elongated main body.

Advantageously, the winding portion at the most distal of the embolization microcatheter, allows a "screw like" motion and thus facilitates advancement of the microcatheter within the blood vessel even in tortuous sections.

Moreover, the three-dimensional structure of the embolization microcatheter, particularly the off-setting of the distal winding portion, as disclosed herein in accordance with some embodiments, advantageously provides a "line-of-sight" of the microcatheter's tip as it progresses through the blood vessel. This may not be facilitated in a standard two-dimensional microcatheter, where the tip section may be hindered by the microcatheter's elongated main body and thus not seen when observing it from a proximal point of view.

Furthermore, the three-dimensional structure of the embolization microcatheter, as disclosed herein in accordance with some embodiments, may advantageously facilitate the securing the microcatheter within the blood vessel by contacting at least two points of the blood vessel wall. Such contact points contribute to the stabilization of the microcatheter in the blood vessel, which is of great importance, particularly during the delivery of embolization beads.

In operation, when the embolization microcatheters, disclosed herein in accordance with some embodiments, is inserted to blood vessel, it progresses in a "screw like" motion facilitated by the winding portion of its distal section. While the user advances the microcatheters within the often small and tortuous blood vessel, the winding portion, which is offset from the elongated main body, can be observed during the procedure. This facilitates navigation of the microcatheter within the blood vessel. During the procedure the user can also utilize the three-dimensional structure of the embolization microcatheter to contact the blood vessel wall at two or more points. This allows stabilization of the microcatheter within the blood vessel and facilitates safer and more accurate performance of the procedure.

According to some embodiments, there is provided an embolization microcatheter comprising an elongated main body and a distal section, the distal section comprising an off-setting portion and a winding portion; wherein the winding portion comprises about half a loop of a three-dimensional spiral, such that a longitudinal axis of the winding portion is offset and/or disposed at an acute angle relative to a longitudinal axis of the elongated main body; wherein the off-setting portion is disposed at an angle of between about 60° and about 120° degrees relative to the longitudinal axis of the elongated main body. According to some embodiments, the winding portion is configured to maneuver the microcatheter longitudinally in a screw-like motion thereby, preventing collapsing, bending kinking, backwards movement, whipping, lashing or any combination thereof of the distal section of the microcatheter. Advantageously, the screw-like motion enables controlled and/or precise steering of the distal section into specific vessels, such as small side branches, which are typically difficult to reach without numerous back and forth movements.

According to some embodiments, the off-setting portion is curved.

According to some embodiments, the longitudinal axis of the winding portion may be offset by between about 0.5 mm and about 5 mm relative to the longitudinal axis of the elongated main body.

According to some embodiments, the acute angle, at which the longitudinal axis of the winding portion is disposed relative to the longitudinal axis of the elongated main body, may be between about 10° and about 60°.

According to some embodiments, the length of the winding portion measures between about 5 mm and about 20 mm. According to some embodiments, the ratio of the length of the winding portion to a radius or mean radius, defined by the half a loop, is between about 2 and about 20.

According to some embodiments, the three-dimensional spiral is right-handed. According to some embodiments, the three-dimensional spiral is left-handed. According to some embodiments, the three-dimensional spiral is a helix.

According to some embodiments, the distal section may be pre-shaped/pre-formed, for example, in the winding/curled/coiled structure.

According to some embodiments, the main body and the off-setting portion together may define a non-planar curve.

According to some embodiments, the elongated main body may further include a filter section including a plurality of side openings formed in a wall of the elongated main body. The side openings may be in the form of slits having a length between about 200 μm and about 800 μm and a width between about 25 μm and about 100 μm.

According to some embodiments, the embolization microcatheter may include a wall having an inner layer, an outer layer, and a skeleton intercalated between the inner layer and the outer layer. According to some embodiments, the outer layer section of the outer layer, on the distal section, may be more flexible than an outer layer section of the outer layer, on the elongated main body.

According to some embodiments, the distal section may be dimensioned such that, when inserted into a tortuous blood vessel, different portions of the distal section contact opposite sides of the tortuous blood vessel at different longitudinal positions of the tortuous blood vessel.

According to some embodiments, the embolization microcatheter may be configured for guide-wire free navigation.

According to some embodiments, the off-set portion is configured to minimize interference of a user's field of view by the winded portion.

According to some embodiments, there is provided a method for performing an embolization procedure, the method includes: inserting to a blood vessel and advancing a embolization microcatheter and performing an embolization procedure wherein the embolization microcatheter includes an elongated main body and a distal section, the distal section comprising an off-setting portion and a winding portion; wherein the winding portion comprises about half a loop of a three-dimensional spiral, such that a longitudinal axis of the winding portion is offset and/or disposed at an acute angle relative to a longitudinal axis of the elongated main body; and wherein the off-setting portion is disposed at an angle of between about 60° and about 120° degrees relative to the longitudinal axis of the elongated main body.

According to some embodiments, there is provided a method for producing an embolization microcatheter distal section that defines a non-planar curve, the method comprising: providing a 3-dimensional mandrel comprising an off-setting portion and a winding portion, wherein the winding portion comprises about half a loop of a three-dimensional spiral, such that a longitudinal axis of the winding portion is offset and/or disposed at an acute angle relative to a longitudinal axis of the elongated main body; and wherein the off-setting portion is disposed at an angle of between about 60° and about 120° degrees relative to the longitudinal axis of the elongated main body; in a heat chamber forming the embolization microcatheter tube on the mandrel, thereby producing the embolization microcatheter having the shape of the mandrel.

Certain embodiments of the present disclosure may include some, all, or none of the above characteristics. One or more technical advantages may be readily apparent to those skilled in the art from the figures, descriptions and claims included herein. Moreover, while specific characteristics have been enumerated above, various embodiments may include all, some or none of the enumerated characteristics.

In addition to the exemplary aspects and embodiments described above, further aspects and embodiments will be further expanded upon in the figures and the following detailed descriptions.

BRIEF DESCRIPTION OF THE FIGURES

The features, nature and advantages of the present disclosure will become more apparent from the detailed description set forth below when taken in conjunction with the drawings in which like reference characters identify correspondingly throughout. Identical structures elements or parts that appear in more than one figure are generally labeled with the same number in all the figures in which they appear. Alternatively, elements or parts that appear in more than one figure may be labeled with different numbers in the different figures in which they appear. The dimensions of the components and features in the figures were chosen for convenience and clarity of presentation and are not necessarily shown to scale. The figures are listed below.

DETAILED DESCRIPTION OF THE INVENTION

Figure 1:
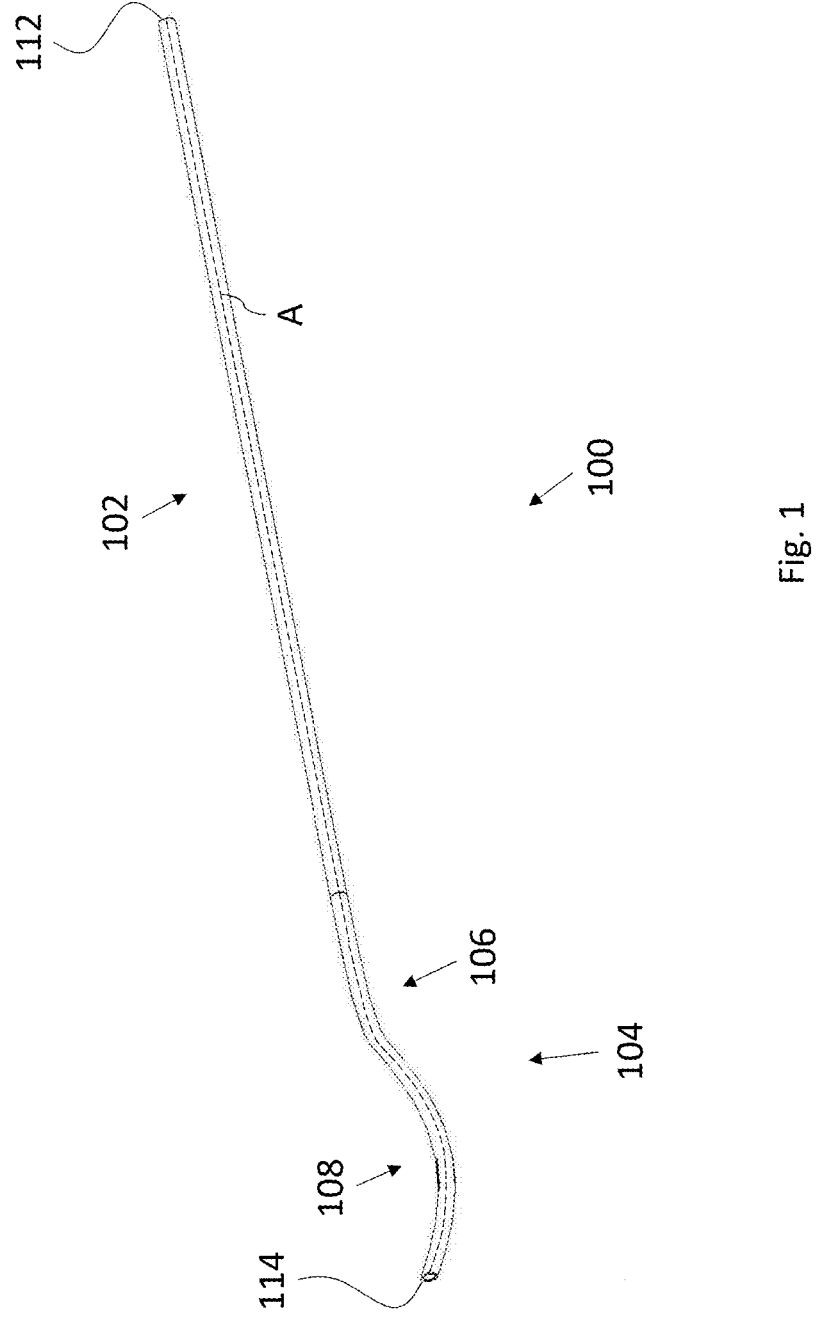
FIG. 1 presents a schematic, perspective view of an embolization microcatheter including an elongated main body and a distal section, according to some embodiments.
Figure 2:
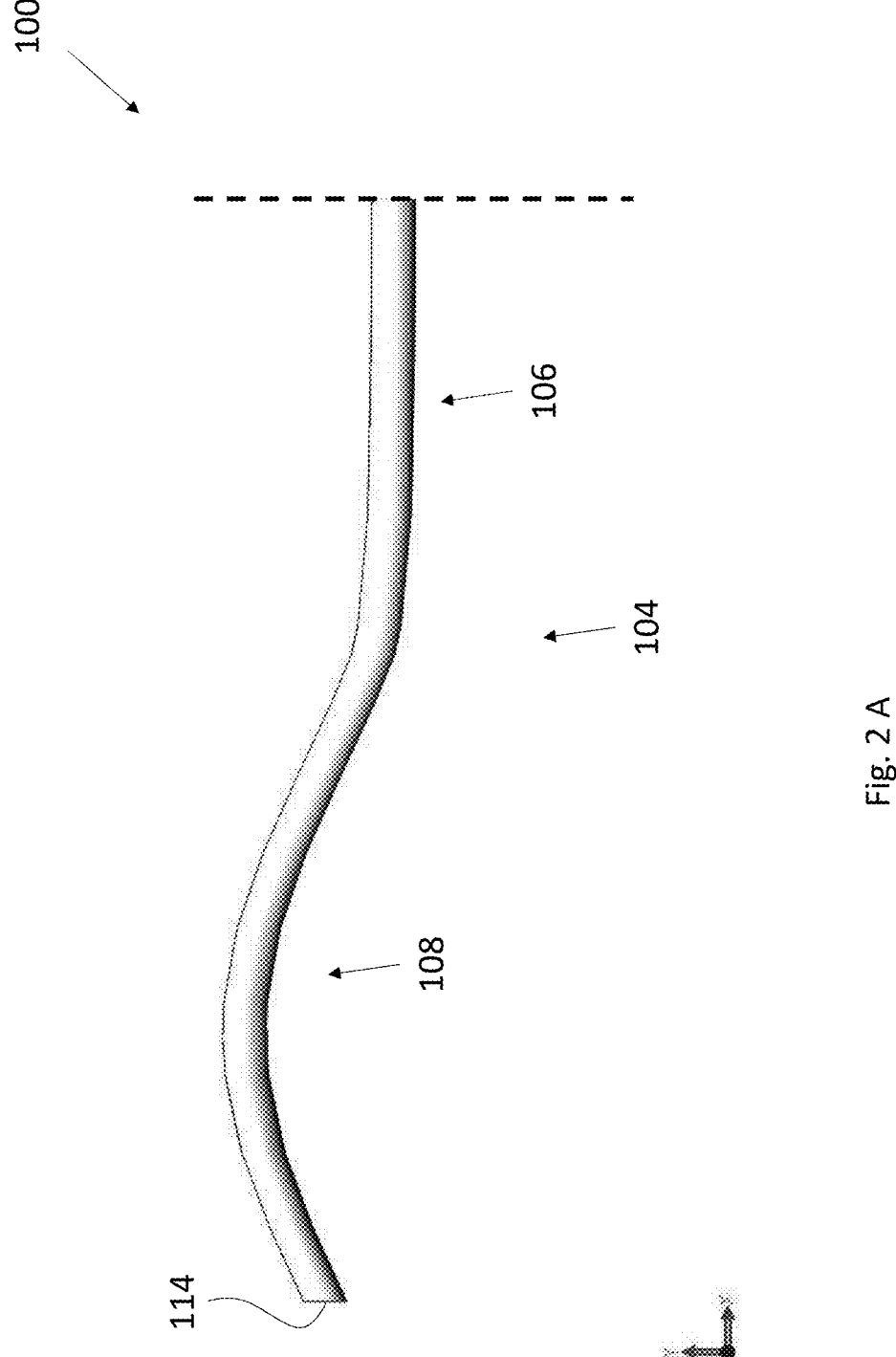
FIG. 2A presents a schematic, side-view of the distal section of the embolization microcatheter of FIG. 1 from a point-of-view directed along the negative z-axis (indicated), according to some embodiments.
FIG. 2B presents a schematic, side-view of the distal section of the embolization microcatheter of FIG. 1 from a point-of-view directed along the positive z-axis, according to some embodiments.
Figure 2:
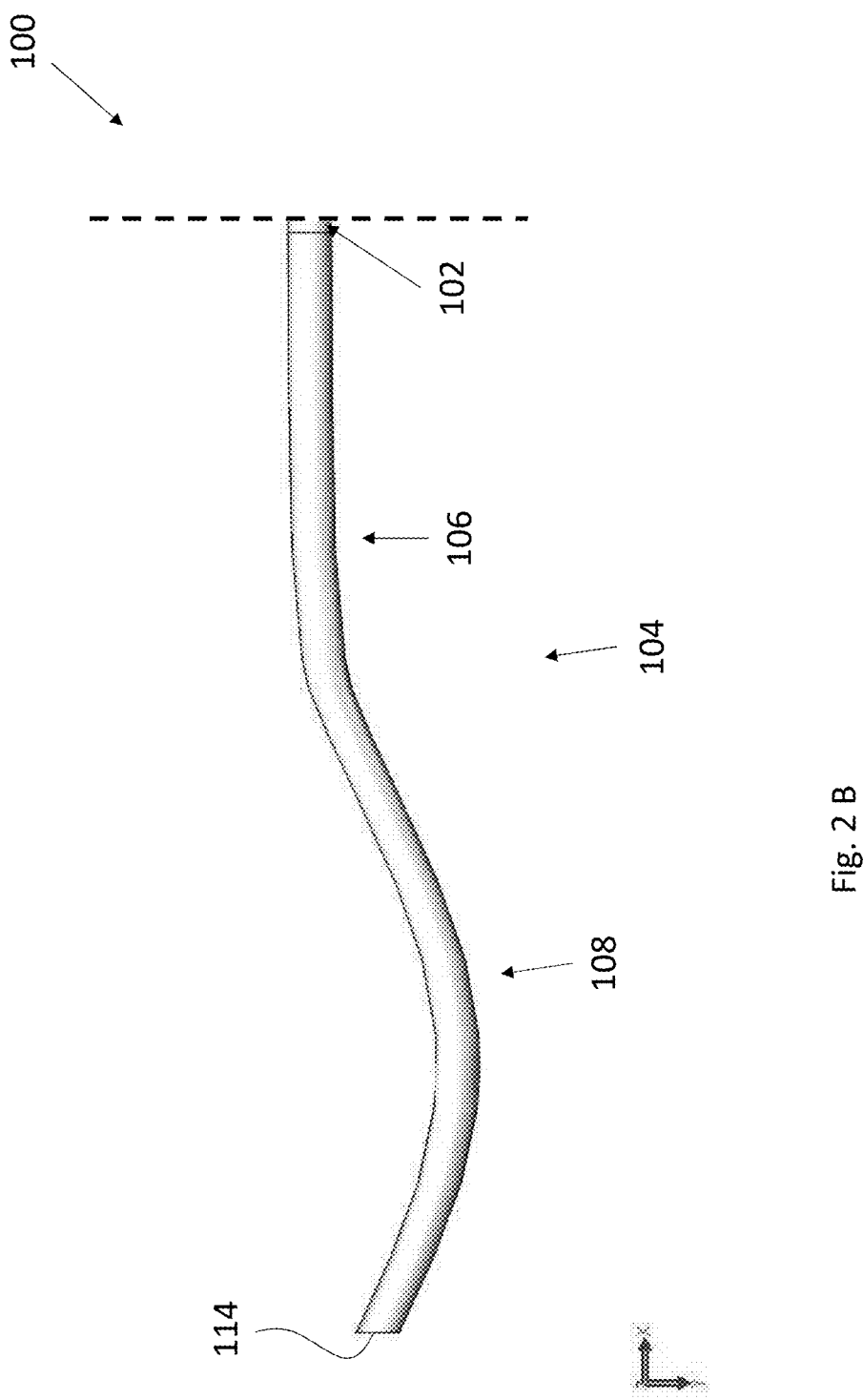
Figure 3:
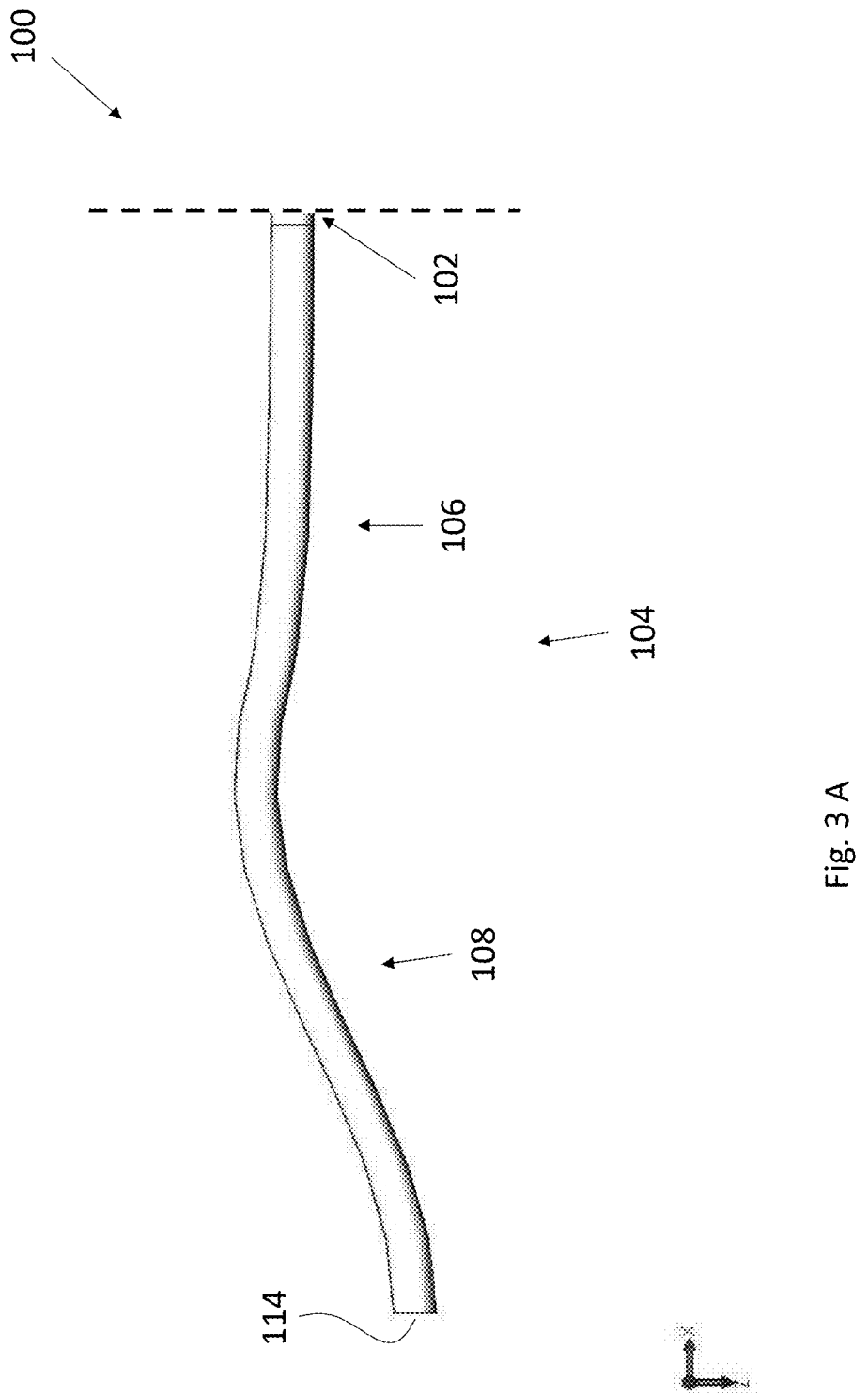
FIG. 3A presents a schematic, side-view of the distal section of the embolization microcatheter of FIG. 1 from a point-of-view directed along the negative y-axis (indicated), according to some embodiments.
FIG. 3B presents a schematic, side-view of the distal section of the embolization microcatheter of FIG. 1 from a point-of-view directed along the positive y-axis, according to some embodiments.
Figure 3:
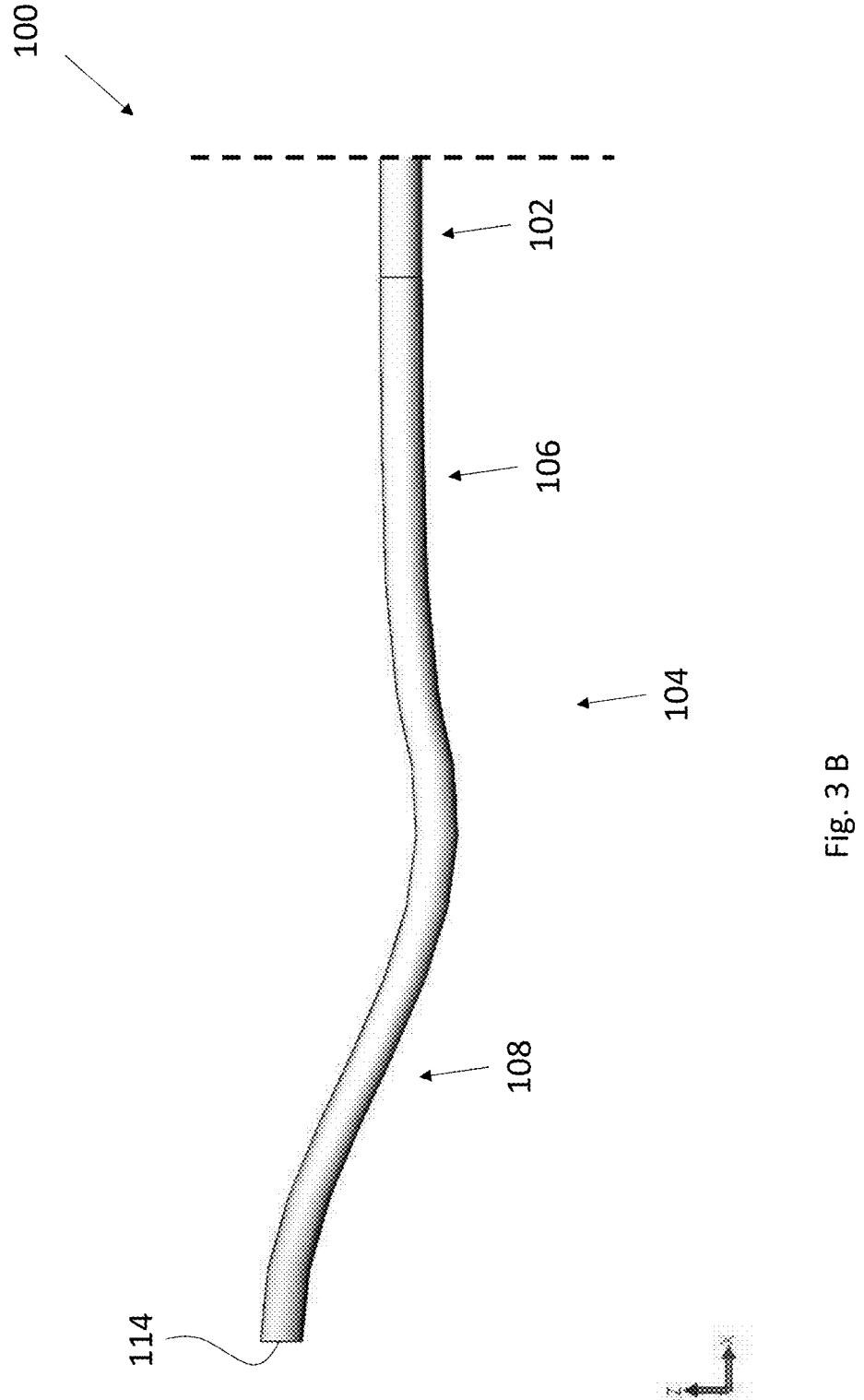
Figure 4:
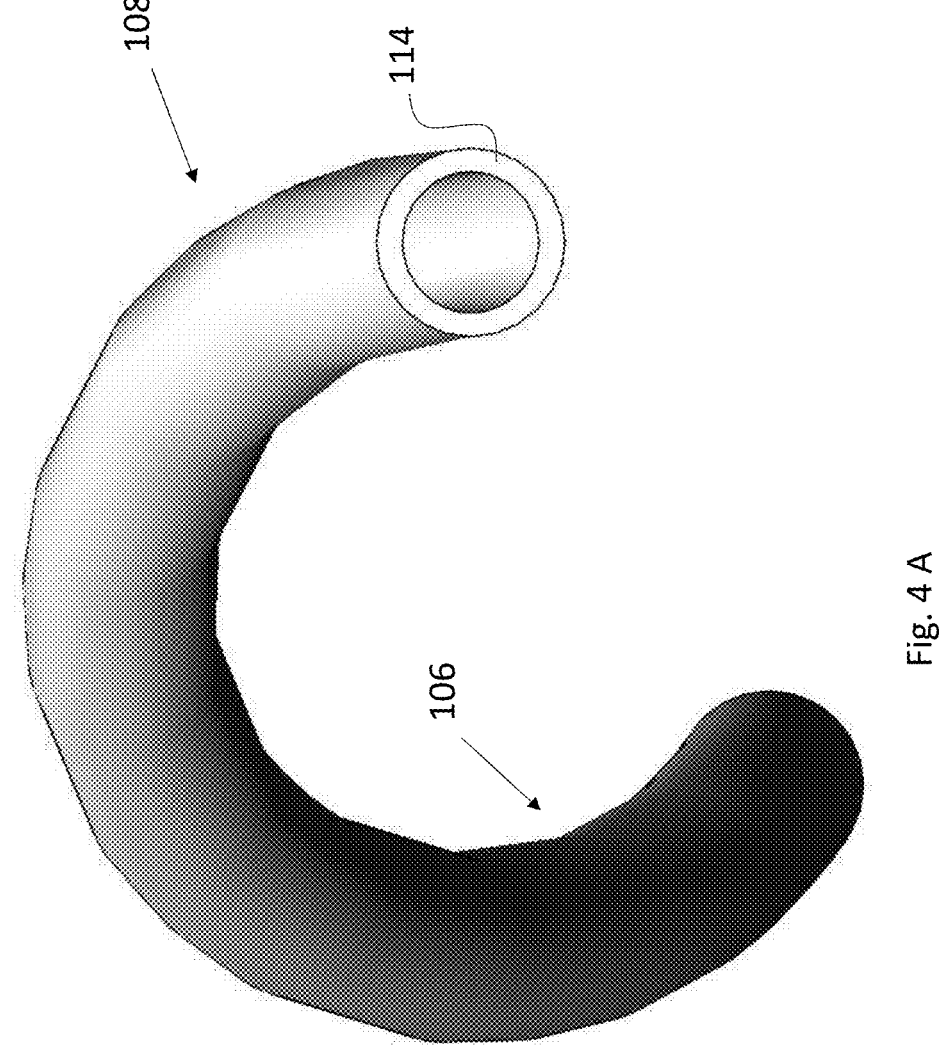
FIG. 4A presents a schematic, front-view of the embolization microcatheter of FIG. 1, according to some embodiments.
FIG. 4B presents a schematic, back-view of the embolization microcatheter of FIG. 1, according to some embodiments.
Figure 4:
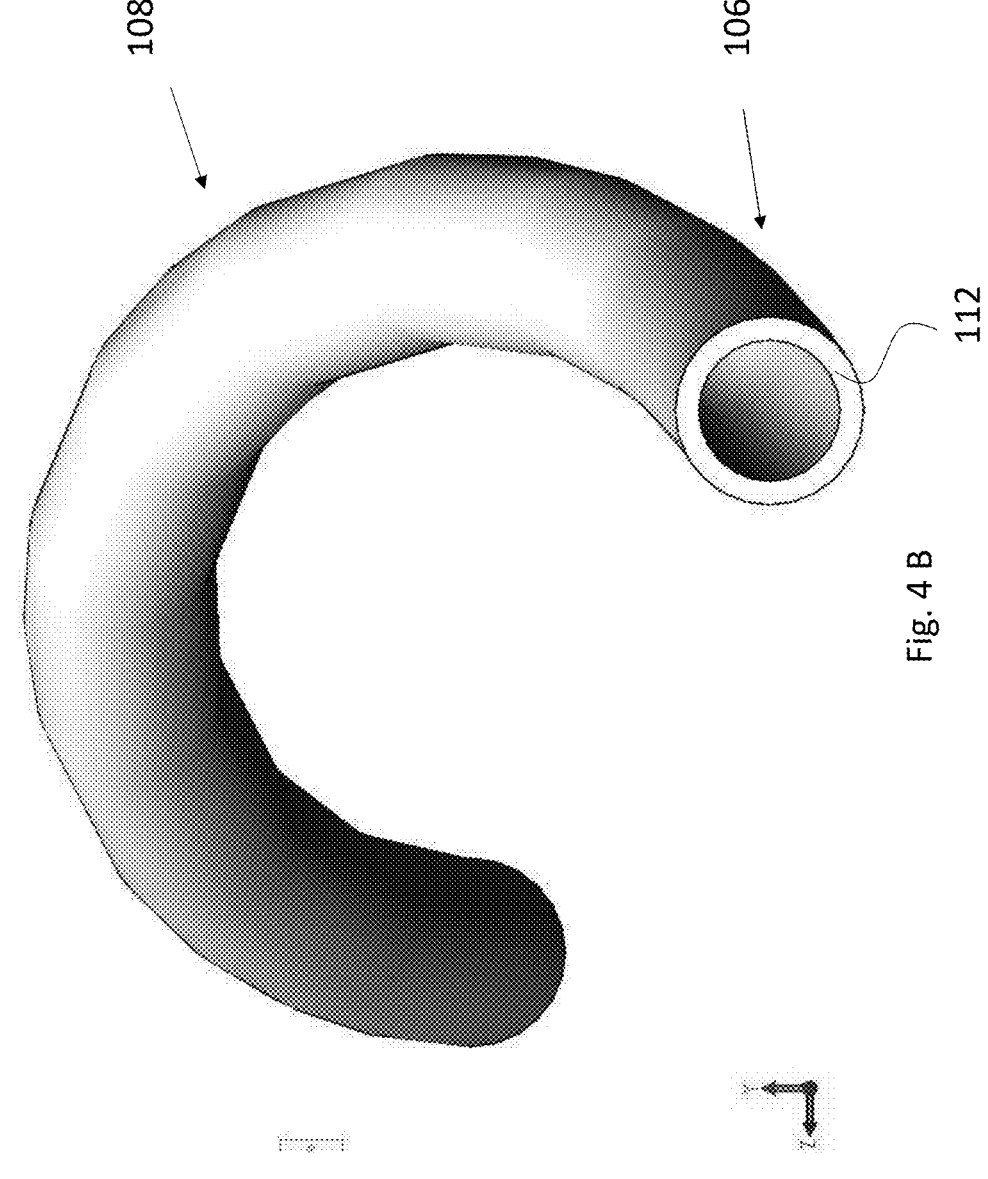
Figure 5:
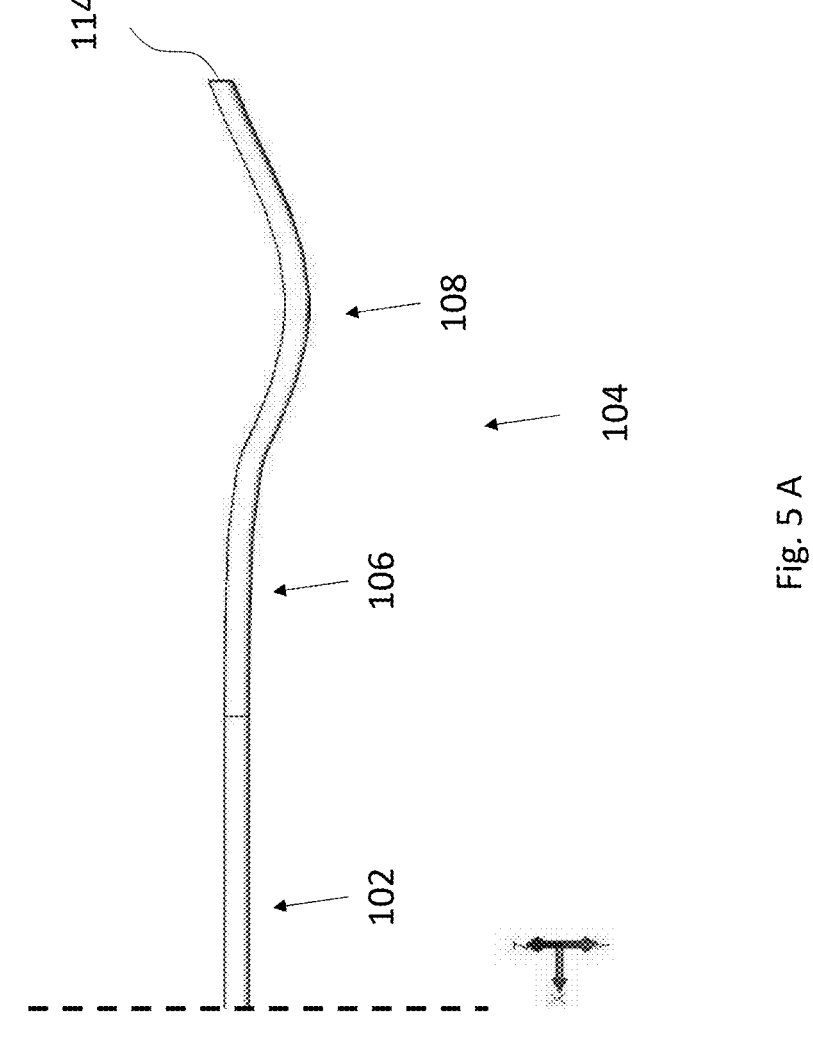
FIG. 5A presents a schematic, side-view of the embolization microcatheter of FIG. 1 from a point-of-view pointing substantially midway along a direction between the negative y-axis and the negative z-axis on the yz-plane, according to some embodiments.
FIG. 5B presents a schematic, side-view of the embolization microcatheter of FIG. 1 from a point-of-view pointing substantially midway along a direction between the positive y-axis and the positive z-axis on the yz-plane, according to some embodiments.
Figure 5:
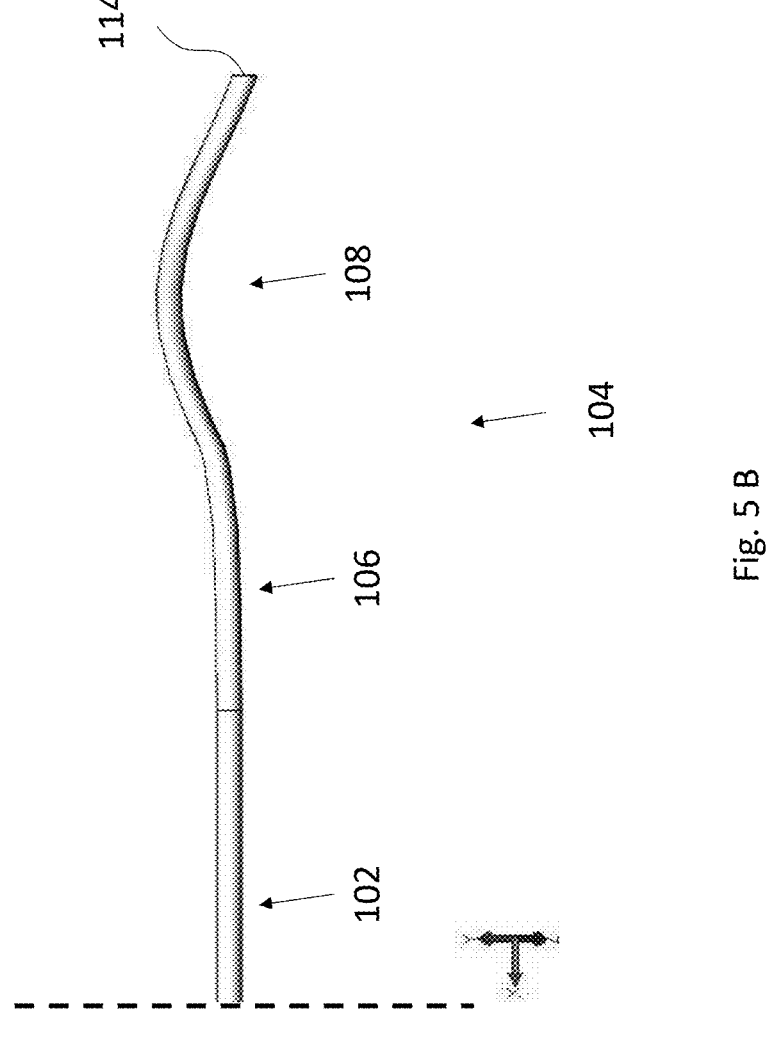
Figure 6:
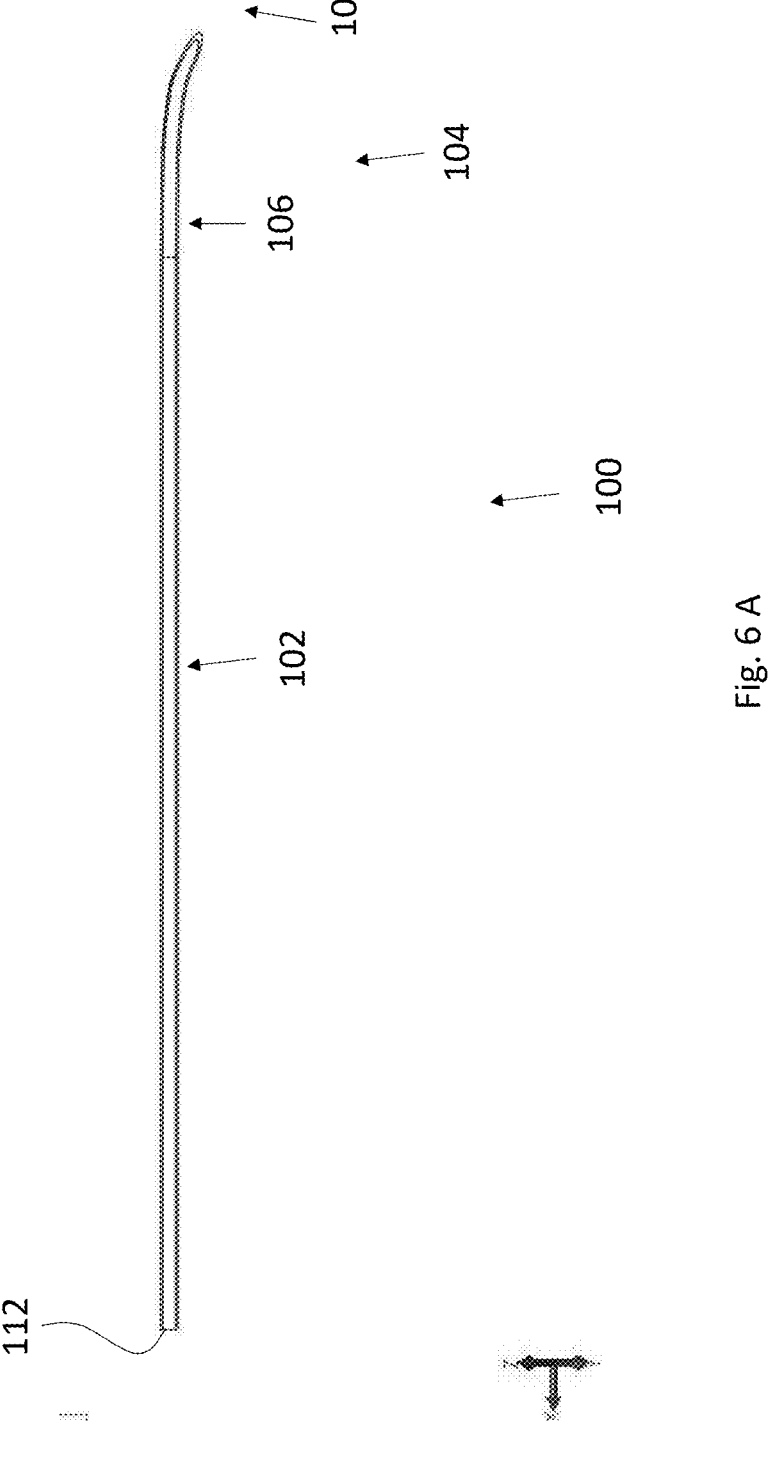
FIG. 6A presents a schematic, cross-sectional view of the embolization microcatheter of FIG. 1 from the point-of-view of FIG. 5A, the cross-section bisects the main body along a plane perpendicular to the direction defined by the point-of-view, according to some embodiments.
FIG. 6B presents a schematic, cross-sectional view of the embolization microcatheter of FIG. 1 from the point-of-view of FIG. 5B, the cross-section bisects the main body along a plane perpendicular to the direction defined by the point-of-view, according to some embodiments.
Figure 6:
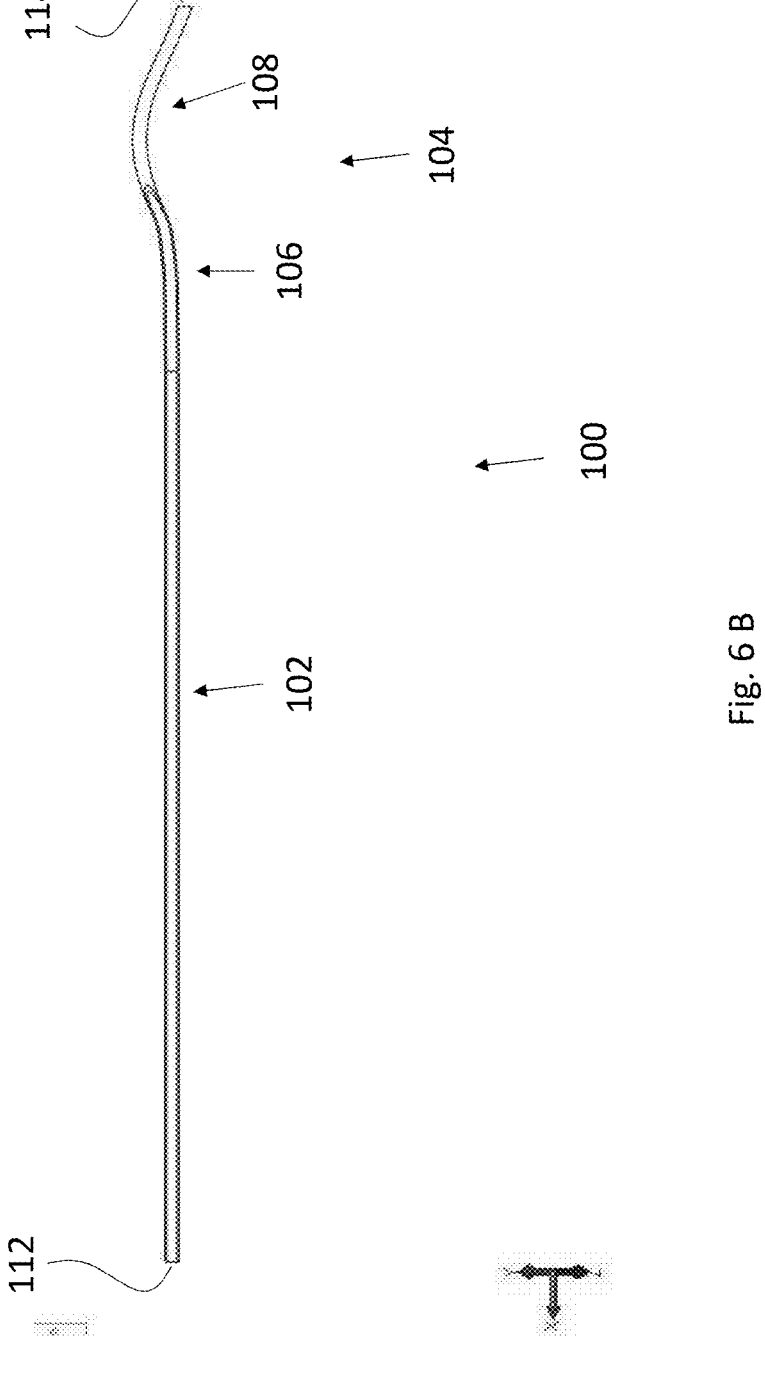

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will also be apparent to one skilled in the art that these concepts may be practiced without specific details being presented herein. In some instances, well-known features may be omitted or simplified in order to avoid obscuring the disclosure.

One of the main challenges of embolization microcatheters is navigation in small and tortuous blood vessels, while also facilitating reliable real time tracking of the microcatheter's advancement during the embolization procedure.

Advantageously, these requirements are met by the herein disclosed microcatheter and its structural characteristics.

There is thus provided herein, in accordance with some embodiments, an embolization microcatheter including an elongated main body and a distal section, the distal section comprising an off-setting portion and a winding portion, wherein the winding portion comprises about half a loop of a three-dimensional spiral, such that a longitudinal axis of the winding portion is offset and/or disposed at an acute angle relative to a longitudinal axis of the elongated main body, and wherein the off-setting portion is disposed at an angle of between about 60° and about 120° degrees (for example, between about 60° and about 80°, between about 80° and about 100° or between about 100° and about 120°, each possibility presets a separate embodiment) relative to the longitudinal axis of the elongated main body. The off-setting portion may be curved.

According to some embodiments, the longitudinal axis of the winding portion may be offset by between about 0.5 mm and about 5 mm (for example, between about 0.5 mm and about 1 mm, between about 1 mm and about 3 mm or between about 3 mm and about 5 mm, each possibility presets a separate embodiment) relative to the longitudinal axis of the elongated main body.

According to some embodiments, the acute angle, at which the longitudinal axis of the winding portion is disposed relative to the longitudinal axis of the elongated main body, is between about 10° and about 60°, for example, between about 10° and about 30°, between about 30° and about 40° or between about 40° and about 60°, each possibility presets a separate embodiment.

According to some embodiments, the length of the winding portion measures between about 5 mm and about 20 mm, for example, between about 5 mm and about 10 mm, between about 10 mm and about 15 mm or between about 15 mm and about 20 mm, each possibility presets a separate embodiment.

According to some embodiments, the ratio of the length of the winding portion to a radius or mean radius, defined by the half a loop, is between about 2 and about 20, for example, between about 2 and about 5, between about 5 and about 10 or between about 10 and about 20, each possibility presets a separate embodiment.

According to some embodiments, the microcatheter 100 may have a length of at least 50 cm, at least 60 cm, at least 75 cm, or at least 1 m. Each possibility is a separate embodiment. Each possibility is a separate embodiment.

According to some embodiments, the three-dimensional spiral may be right-handed. According to some embodiments, the three-dimensional spiral may be left-handed. According to some embodiments, the three-dimensional spiral may be a helix. According to some embodiments, the distal section may be pre-shaped.

According to some embodiments, the main body and the off-setting portion together define a non-planar curve.

According to some embodiments, the elongated main body may further include a filter section, which includes a plurality of side openings formed in a wall of the elongated main body. The side openings may be in the form of slits having a length between about 200 μm and about 800 μm and a width between about 25 μm and about 100 μm, for example, having a length between about 200 μm and about 300 μm and a width between about 75 μm and about 100 μm, or having a length between about 600 μm and about 800 μm and a width between about 25 μm and about 50 μm or having a length between about 500 μm and about 800 μm and a width between about 50 μm and about 100 μm or having a length between about 200 μm and about 400 μm and a width between about 25 μm and about 50 μm, each possibility presets a separate embodiment.

According to some embodiments, the embolization microcatheter has a wall, which includes an inner layer, an outer layer, and a skeleton intercalated between the inner layer and the outer layer. An outer layer section of the outer layer, on the distal section, may be more flexible than an outer layer section of the outer layer, on the elongated main body.

According to some embodiments, the distal section may be dimensioned such that, when inserted into a tortuous blood vessel, different portions of the distal section contact opposite sides of the tortuous blood vessel at different longitudinal positions of the tortuous blood vessel.

As used herein, the terms "embolization", "transcatheter embolization", "transcatheter arterial embolization" and "TAE" may be used interchangeably and refer to the passage and lodging of an embolus within the bloodstream for therapeutic purposes, for example, as a hemostatic treatment of bleeding or as a treatment for some types of cancer by deliberately blocking blood vessels to starve the tumor cells.

As used herein, in accordance with some embodiments, the term "winding portion" may refer to a section of the microcatheter having a non-straight, curved, twisted, bent, spiral, coiled and/or partially coiled shape and/or having one or more loops/partial loops.

As used herein, in accordance with some embodiments, the term "off-setting portion" may refer to a section of the microcatheter connecting between the elongated main body and the winding portion of the microcatheter and shaped to create an offset and/or an (acute) angle between the longitudinal axis of the winding portion and the longitudinal axis of the elongated main body.

Reference is now made to FIG. 1, which presents a schematic, perspective view of an embolization microcatheter 100 including an elongated main body 102 and a distal section 104, according to some embodiments. Distal section 104 includes an off-setting portion 106 and a winding portion 108. Embolization microcatheter 100 extends from a proximal end opening 112 to a distal end opening 114.

As used herein, the terms "distal end opening" and "proximal end opening" refer to the end openings of the microcatheter leading into the lumen thereof.

Dashed line "A" represents a central longitudinal axis of embolization microcatheter 100 extending from elongated main body 102 and distal section 104, which includes off-setting portion 106 and winding portion 108.

Off-setting portion 106 is disposed at an angle (for example, of between about 60° and about 120° degrees) relative to the longitudinal axis of elongated main body 102 and winding portion 108 forms about half a loop of a three-dimensional spiral, such that the longitudinal axis of winding portion 108 is offset relative to the longitudinal axis of elongated main body 102.

Reference is now made to FIGS. 2A-6B, which present various views of embolization microcatheter 100, therefore the elements or parts numbers of FIG. 1 apply to the same elements or parts of FIGS. 2A-6B.

FIG. 2A presents a schematic, side-view of the distal section of embolization microcatheter 100 of FIG. 1 from a point-of-view directed along the negative z-axis (indicated), according to some embodiments. It is noted that off-setting portion 106 (and elongated main body 102) continues beyond the dashed vertical line but is not shown in the figure.

FIG. 2B presents a schematic, side-view of the distal section of embolization microcatheter 100 of FIG. 1 from a point-of-view directed along the positive z-axis (indicated), according to some embodiments. It is noted that elongated main body 102 continues beyond the dashed vertical line but is not shown in the figure.

FIG. 3A presents a schematic, side-view of the distal section of embolization microcatheter 100 of FIG. 1 from a point-of-view directed along the negative y-axis (indicated), according to some embodiments. It is noted that elongated main body 102 continues beyond the dashed vertical line but is not shown in the figure.

FIG. 3B presents a schematic, side-view of the distal section of embolization microcatheter 100 of FIG. 1 from a point-of-view directed along the positive y-axis (indicated), according to some embodiments, according to some embodiments. It is noted that elongated main body 102 continues beyond the dashed vertical line but is not shown in the figure.

FIG. 4A presents a schematic, front-view (looking towards distal end opening 114) of the embolization microcatheter 100 of FIG. 1, according to some embodiments.

FIG. 4B presents a schematic, back-view (looking towards proximal end opening 112) of the embolization microcatheter 100 of FIG. 1, according to some embodiments. It is noted that in this point of view, elongated main body 102 cannot be seen as it is "hidden" behind proximal end opening 112, while only off-setting portion 106 and winding portion 108 are visible.

FIG. 5A presents a schematic, side-view of embolization microcatheter 100 of FIG. 1 from a point-of-view pointing substantially midway along a direction between the negative y-axis and the negative z-axis on the yz-plane, according to some embodiments. It is noted that elongated main body 102 continues beyond the dashed vertical line but is not shown in the figure.

FIG. 5B presents a schematic, side-view of the embolization microcatheter of FIG. 1 from a point-of-view pointing substantially midway along a direction between the positive y-axis and the positive z-axis on the yz-plane, according to some embodiments. It is noted that elongated main body 102 continues beyond the dashed vertical line but is not shown in the figure.

FIG. 6A presents a schematic, cross-sectional view of embolization microcatheter 100 of FIG. 1 from the point-of-view of FIG. 5A, the cross-section bisects the main body along a plane perpendicular to the direction defined by the point-of-view, according to some embodiments. It is noted that in this cross-sectional point of view, winding portion 108 (or at least a portion thereof) is not visible due to its angle.

FIG. 6B presents a schematic, cross-sectional view of embolization microcatheter 100 of FIG. 1 from the point-of-view of FIG. 5B, the cross-section bisects the main body along a plane perpendicular to the direction defined by the point-of-view, according to some embodiments. In this cross-sectional point of view, as opposed to the cross-sectional point of view of FIG. 6A, winding portion 108 is not visible, however, not cross-sectioned.

Reference is now made to FIGS. 7-11, which present experimental results demonstrating the better performance of the embolization microcatheter disclosed herein according to some embodiments (designated by the name of "Drakon") in comparison to other embolization microcatheters.

Figure 7:
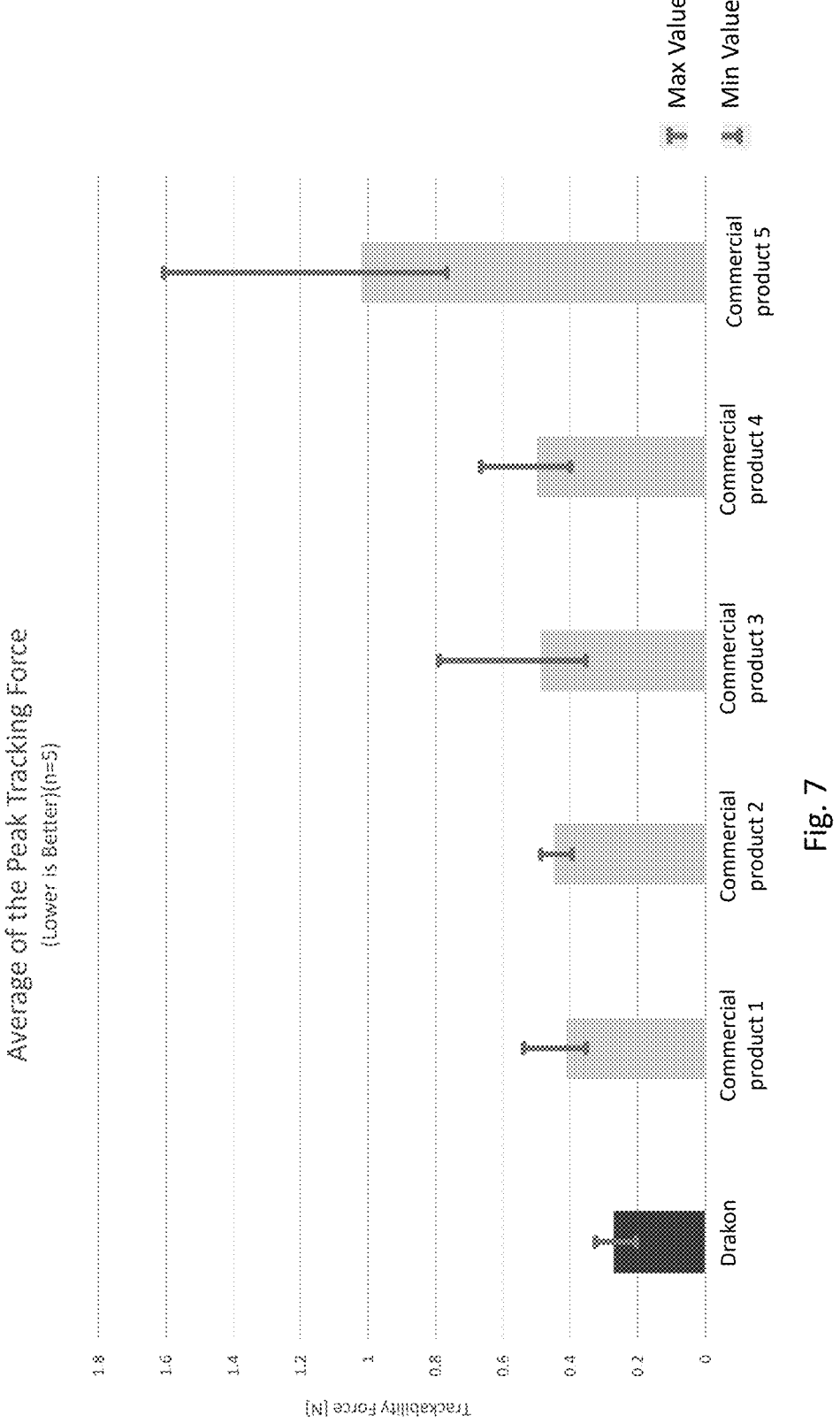
FIG. 7 presents a histogram of the average peak tracking force of the embolization microcatheter disclosed herein according to some embodiments (designated by the name of "Drakon"), in comparison to other embolization microcatheter.

FIG. 7 presents a histogram of the average peak tracking force of the embolization microcatheter disclosed herein according to some embodiments (designated by the name of "Drakon"), in comparison to other embolization microcatheters (Test Protocol RD-039; n=5). The lowest trackability force [N] is obtained for the Drakon compared to other commercial embolization microcatheters, designated as commercial products 1-5. The lower trackability force is indicative of better maneuverability.

Figure 8:
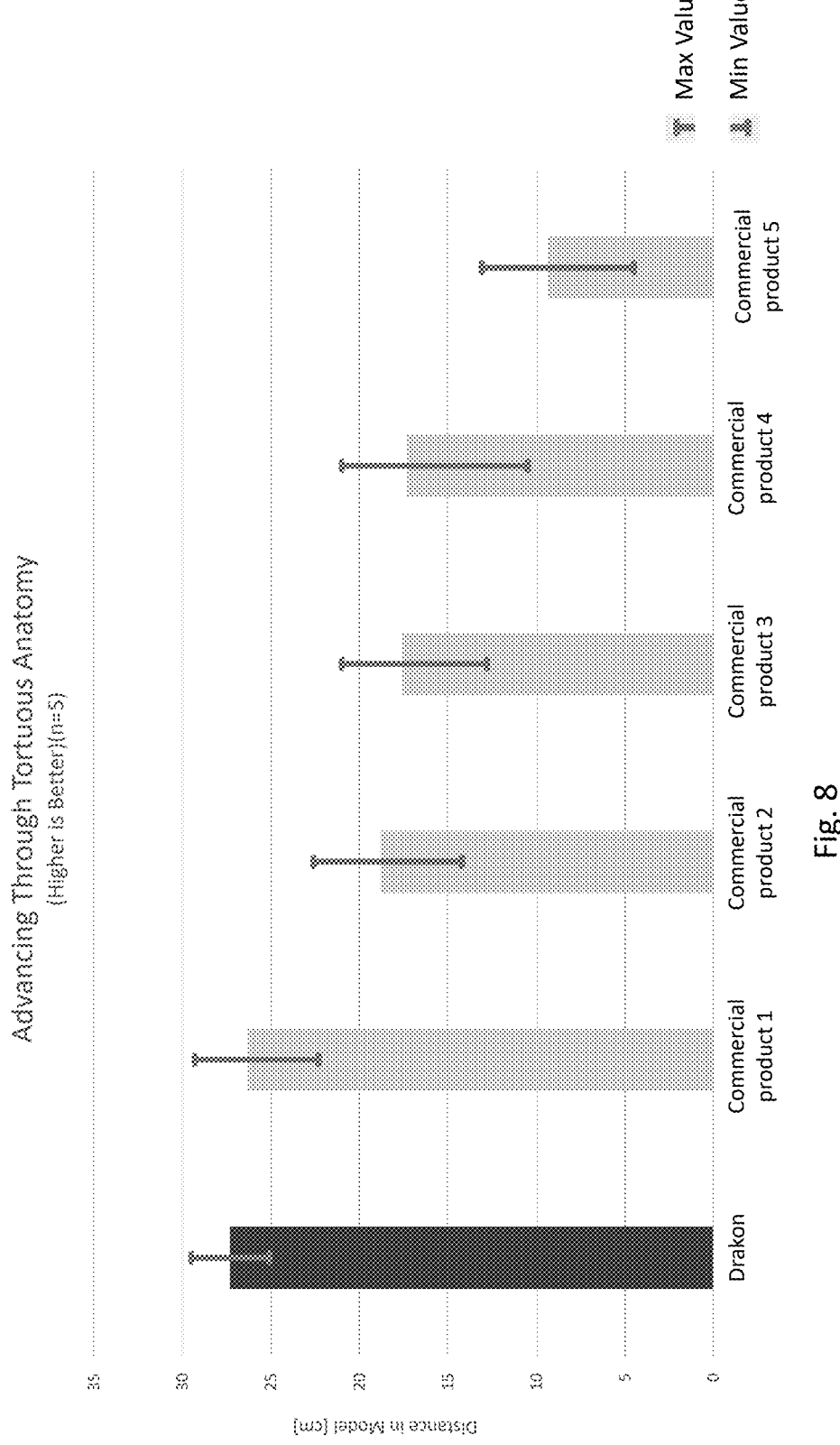
FIG. 8 presents a histogram of the advancing distance through tortuous anatomy achieved by the embolization microcatheter disclosed herein according to some embodiments (designated by the name of "Drakon"), in comparison to other embolization microcatheter.

FIG. 8 presents a histogram of the advancing distance through tortuous anatomy achieved by the embolization microcatheter disclosed herein according to some embodiments (designated by the name of "Drakon"), in comparison to other commercial embolization microcatheters (Test Protocol RD-055; n=5). It can be seen that the Drakon embolization microcatheter is capable of advancing in tortuous anatomy (model) farther than the other microcatheters tested.

Figure 9:
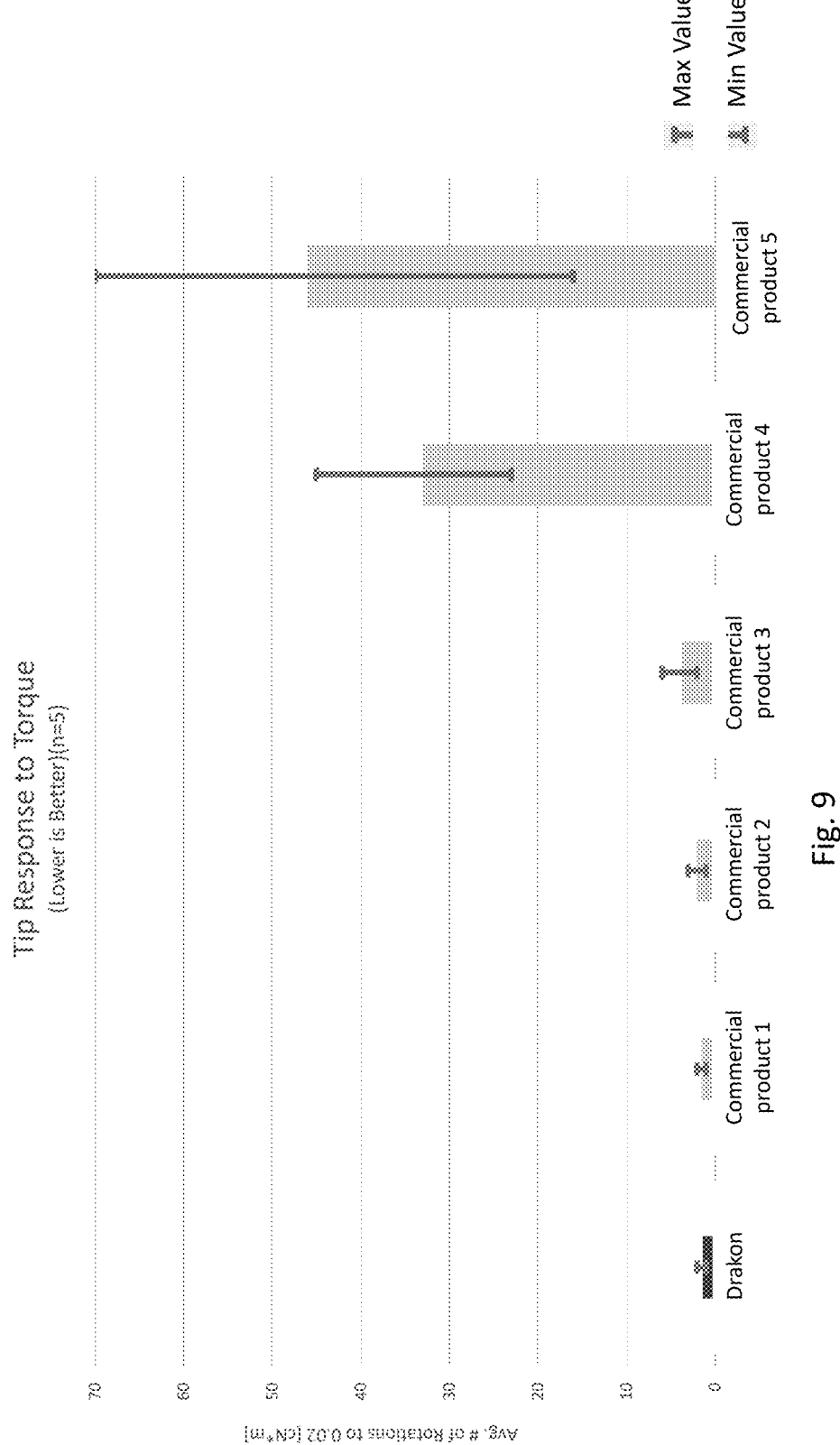
FIG. 9 presents a histogram of the tip response to torque of the embolization microcatheter disclosed herein according to some embodiments (designated by the name of "Drakon"), in comparison to other embolization microcatheter.

FIG. 9 presents a histogram of the tip response to torque of the embolization microcatheter disclosed herein according to some embodiments (designated by the name of "Drakon"), in comparison to other commercial embolization microcatheters (Test Protocol RD-018; n=5). As can be seed from the histogram, the Dragon shows the lowest tip response to torque, measures by the average number of rotations to 0.02 cN*m.

As used herein, the terms "approximately" and "about" refer to +/−10%, or +/−5%, or +−2% vis-à-vis the range to which it refers. Each possibility is a separate embodiment.

While a number of exemplifying aspects and embodiments have been discussed above, those of skill in the art will envisage certain modifications, additions and subcombinations thereof. It is therefore intended that the following appended claims and claims hereafter introduced be interpreted to include all such modifications, additions and sub-combinations as are within their true spirit and scope.

What is claimed is:

1. An embolization microcatheter comprising an elongated main body and a distal section, the distal section comprising an off-setting portion and a winding portion;

wherein the winding portion comprises about half a loop of a three-dimensional spiral, such that a longitudinal axis of the winding portion is offset and/or disposed at an acute angle relative to a longitudinal axis of the elongated main body;

wherein the off-setting portion is disposed at an angle of between about 60° and about 120° degrees relative to the longitudinal axis of the elongated main body, and wherein the winding portion is configured to maneuver the microcatheter longitudinally in a screw-like motion thereby preventing collapsing and/or vibrating and/or whipping of the distal section of the microcatheter, and wherein the embolization microcatheter has an average peak tracking force of less than 0.4 N.

2. The embolization microcatheter of claim 1, wherein the off-setting portion is curved.

3. The embolization microcatheter of claim 1, wherein the longitudinal axis of the winding portion is offset by between about 0.5 mm and about 5 mm relative to the longitudinal axis of the elongated main body.

4. The embolization microcatheter of claim 1, wherein the acute angle, at which the longitudinal axis of the winding portion is disposed relative to the longitudinal axis of the elongated main body, is between about 10° and about 60°.

5. The embolization microcatheter of claim 1, wherein a length of the winding portion measures between about 5 mm and about 20 mm.

6. The embolization microcatheter of claim 1, wherein a ratio of the length of the winding portion to a radius or mean radius, defined by the half a loop, is between about 2 and about 20.

7. The embolization microcatheter of claim 1, wherein the three-dimensional spiral is right-handed.

8. The embolization microcatheter of claim 1, wherein the three-dimensional spiral is left-handed.

9. The embolization microcatheter of claim 1, wherein the three-dimensional spiral is a helix.

10. The embolization microcatheter of claim 1, wherein the distal section is pre-shaped.

11. The embolization microcatheter of claim 1, wherein the main body and the offsetting portion together define a non-planar curve.

12. The embolization microcatheter of claim 1, wherein the elongated main body further comprises a filter section comprising a plurality of side openings formed in a wall of the elongated main body.

13. The embolization microcatheter of claim 12, wherein the side openings are in the form of slits having a length between about 200 μm and about 800 μm and a width between about 25 μm and about 100 μm.

14. The embolization microcatheter of claim 1, comprising a wall comprising an inner layer, an outer layer, and a skeleton intercalated between the inner layer and the outer layer.

15. The embolization microcatheter of claim 14, wherein an outer layer section of the outer layer, on the distal section, is more flexible than an outer layer section of the outer layer, on the elongated main body.

16. The embolization microcatheter of claim 1, wherein the distal section is dimensioned such that, when inserted into a tortuous blood vessel, different portions of the distal section contact opposite sides of the tortuous blood vessel at different longitudinal positions of the tortuous blood vessel.

17. The embolization microcatheter of claim 1, configured for guide-wire free navigation.

18. The embolization microcatheter of claim 1, wherein the off-set portion is configured to minimize interference of a user's field of view by the winded portion.

19. A method for producing an embolization microcatheter distal section that defines a non-planar curve, the method comprising:

providing a 3-dimensional mandrel comprising an off-setting portion and a winding portion, wherein the winding portion comprises about half a loop of a three-dimensional spiral, such that a longitudinal axis of the winding portion is offset and/or disposed at an acute angle relative to a longitudinal axis of the elongated main body; and wherein the off-setting portion is disposed at an angle of between about 60° and about 120° degrees relative to the longitudinal axis of the elongated main body;

in a heat chamber forming the embolization microcatheter tube on the mandrel, thereby producing the embolization microcatheter having the shape of the mandrel.

* * * * *